United States Patent [19]
Day et al.

[11] Patent Number: 5,218,656
[45] Date of Patent: Jun. 8, 1993

[54] OPTICAL FIBER PROBE FOR ATTENTUATED TOTAL REFLECTANCE MEASUREMENTS

[75] Inventors: Leslie L. Day, Caterham; Graham Poulter, Orpington, both of England

[73] Assignee: Specac Ltd., Orpington, England

[21] Appl. No.: 664,583

[22] Filed: Mar. 4, 1991

[51] Int. Cl.⁵ .............................................. G02B 6/36
[52] U.S. Cl. ...................................................... 385/47
[58] Field of Search ............... 350/96.10, 96.15, 96.18, 350/96.20, 96.29

[56] References Cited

U.S. PATENT DOCUMENTS

| | | | |
|---|---|---|---|
| 4,156,556 | 5/1979 | Klein et al. | 350/96.15 |
| 4,329,017 | 5/1982 | Kapany et al. | 385/47 X |
| 4,422,714 | 12/1983 | Benoit et al. | 385/47 X |
| 4,486,071 | 12/1984 | Levinson | 385/47 X |
| 4,684,208 | 8/1987 | Ishikawa et al. | 385/47 X |
| 4,735,478 | 4/1988 | Hily et al. | 385/47 |
| 4,836,634 | 6/1989 | Laude | 385/47 X |
| 4,904,043 | 2/1990 | Schweizer | 350/96.15 X |
| 4,932,742 | 6/1990 | Tohme | 350/96.18 |
| 4,938,554 | 7/1990 | Wilson et al. | 350/96.15 |
| 4,938,555 | 7/1990 | Savage | 350/96.15 |
| 4,989,932 | 2/1991 | Landa et al. | 350/96.15 X |
| 5,051,551 | 9/1991 | Doyle | 250/341 |

Primary Examiner—Akm E. Ullah
Attorney, Agent, or Firm—Wallenstein, Wagner & Hattis, Ltd.

[57] ABSTRACT

An optical fiber probe for attenuated total reflectance measurements comprises a tubular body within which pass input and output optical fibers. The optical fibers are mounted within the body so that radiation emitted from the end of one of the optical fibers can pass through the optical system of the probe and be reflected back and focused on to the end of the other optical fiber for transmission back to a spectrophotometer. The optical system includes an attenuated total reflectance element, preferably of zinc selenide, which has a cylindrical body having at one end two perpendicular cut-away surfaces to form a roof mirror and at the other end a convex surface which acts to focus the radiation on to the end of the output optical fiber. The material to be tested is allowed to come into contact with the surfaces of the roof mirror, and then radiation is sent through the element and is totally internally reflected within it. Sealing around the element is effected by means of an O ring seal which extends around the element's cylindrical surface. Since there are no internal reflections from this surface, the spectrum of the O ring is not picked up.

33 Claims, 9 Drawing Sheets

OPTICAL FIBER PROBE FOR ATTENTUATED TOTAL REFLECTANCE MEASUREMENTS

FIELD OF THE INVENTION

The present invention relates to optical fiber probes for remote analysis, and particularly for probes for use with spectrophotometers. Probes of this type permit the analysis of materials remote from the spectrophotometer, for example storage containers or in on-line process plant, thus removing the need to bring samples to the spectrophotometer and simplifying and speeding analysis. In particular, the present invention relates to a novel optical element for example for an attenuated total reflectance optical fiber probe. The novel optical element could be used in other applications, for example in a pressure cell, and the invention extends to not only a probe having such an element but also to the element per se.

DISCUSSION OF THE PRIOR ART

Attentuated total reflectance of ATR probes have been known for some time, and various geometries of optical elements for such probes have been proposed for example by N.J. Harrick in "Internal Reflection Spectroscopy" (Harrick Scientific Corporation, New York 1979).

In most of the currently known devices, the optical element is shaped so that radiation enters through one face, passes along the element and exits through another face. In between the entrance and exit, the radiation makes a number of total internal reflections from the side walls of the element, the total internal reflections causing the radiation to pick up the spectrum of a sample material which is in contact with the optical element at the points where total internal reflection occurs.

Elements of this type are difficult to construct, as they generally have to be square or rectangular in cross-section, and this also makes them difficult to seal around. Since the liquid to be tested has to be in contact with at least some of the surfaces of the optical element but must not be allowed to enter the interior of the probe, some sort of seal has to be provided. Because of the shape of the optical elements, special machined seals have to be provided, this being expensive. Normal O-ring seals cannot of course be used with square or rectangular sectioned elements and it is not always possible to make these elements circular in section so as to enable standard O-ring seals to be utilised.

A further disadvantage with this prior art type of probe is that the seal invariably comes into contact with the optical element on the surfaces where total internal reflections are occurring. This causes the spectrum of the seal itself to be picked up by the radiation, and combined with the spectrum of the sample liquid under test. This is obviously undesirable, because the spurious spectrum then has to be subtracted out before the test spectrum can be obtained. Furthermore, the spectrum arising from the seal itself is likely to vary with temperature, and this means that in practice the subtraction is difficult and can only be carried out accurately if the probe has been calibrated for a range of temperatures.

SUMMARY OF THE INVENTION

It is an object of the present invention at least to alleviate the problems of the prior art.

The optical fiber probe of the present invention comprises a tubular sleeve member extending longitudinally of which there are input and output optical fibers. The ends of both optical fibers are held within the probe at spaced positions, preferably with the ends lying in the same plane. Radiation emitted from the end of one of the fibers passes in through the end surface of a radiation-transparent optical element, is totally internally reflected in that element and is redirected back out through the end surface and focused on to the end of the other optical fiber for transmission back to the spectrophotometer.

The optical element itself is desirably circular in section and has a cylindrical side wall, a flat or slightly convex end face and, opposite that end face, a pair of angled reflecting surfaces meeting at a central ridge. The angle at the ridge is preferably 90°. The invention further extends to the optical element per se.

DESCRIPTION OF THE PREFERRED EMBODIMENT

Figure 2:
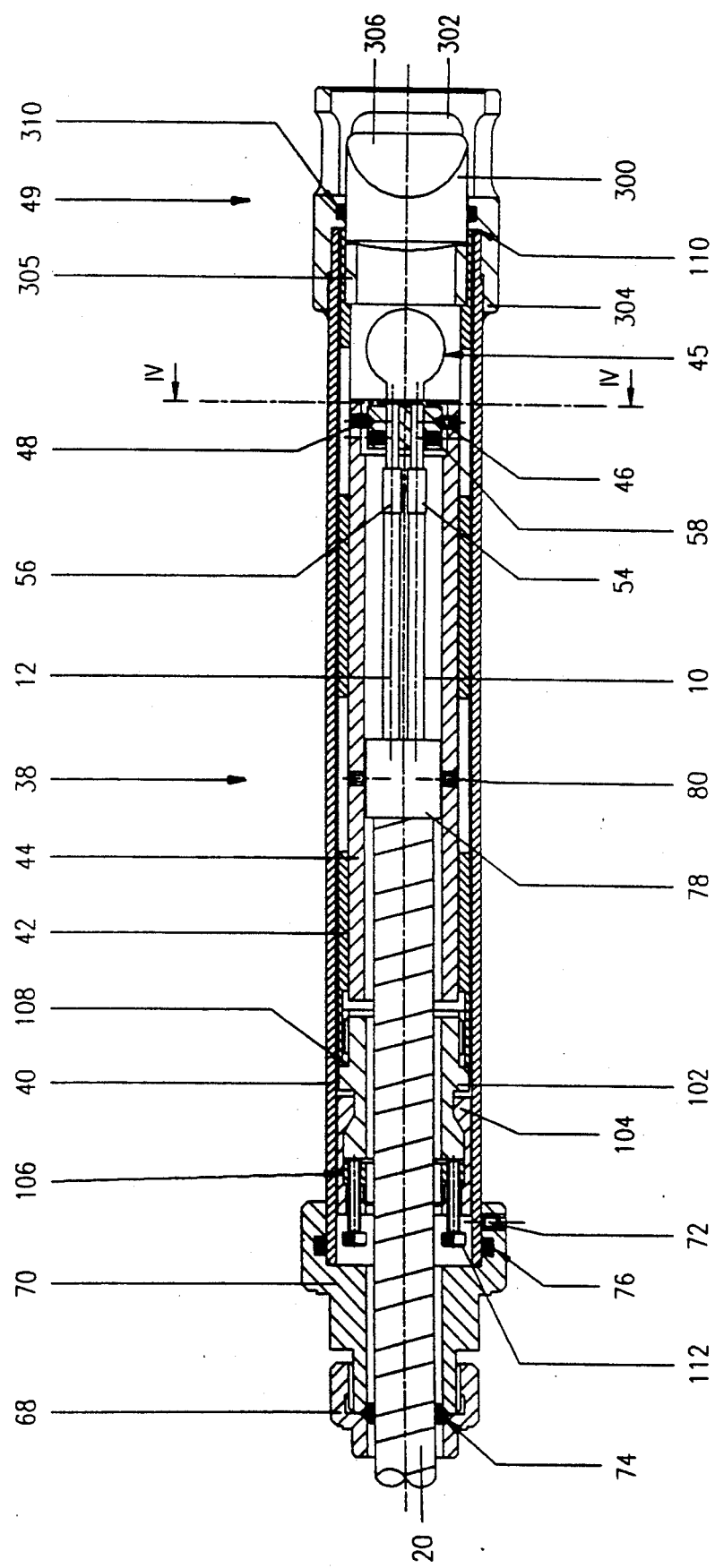
FIG. 2 is a longitudinal section through an optical fiber probe embodying the present invention.
Figure 3:
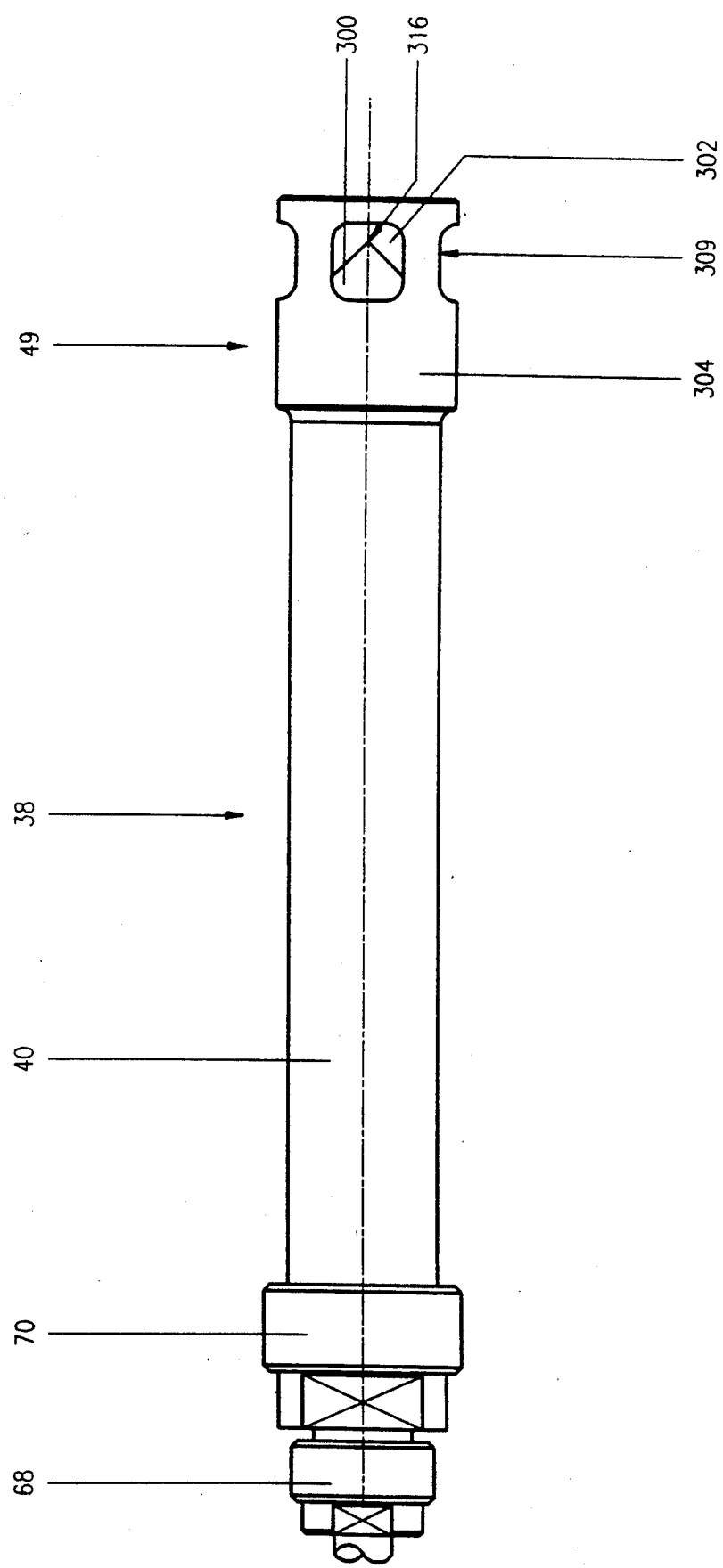
FIG. 3 is a side elevation of the probe of FIG. 2.
Figure 4:
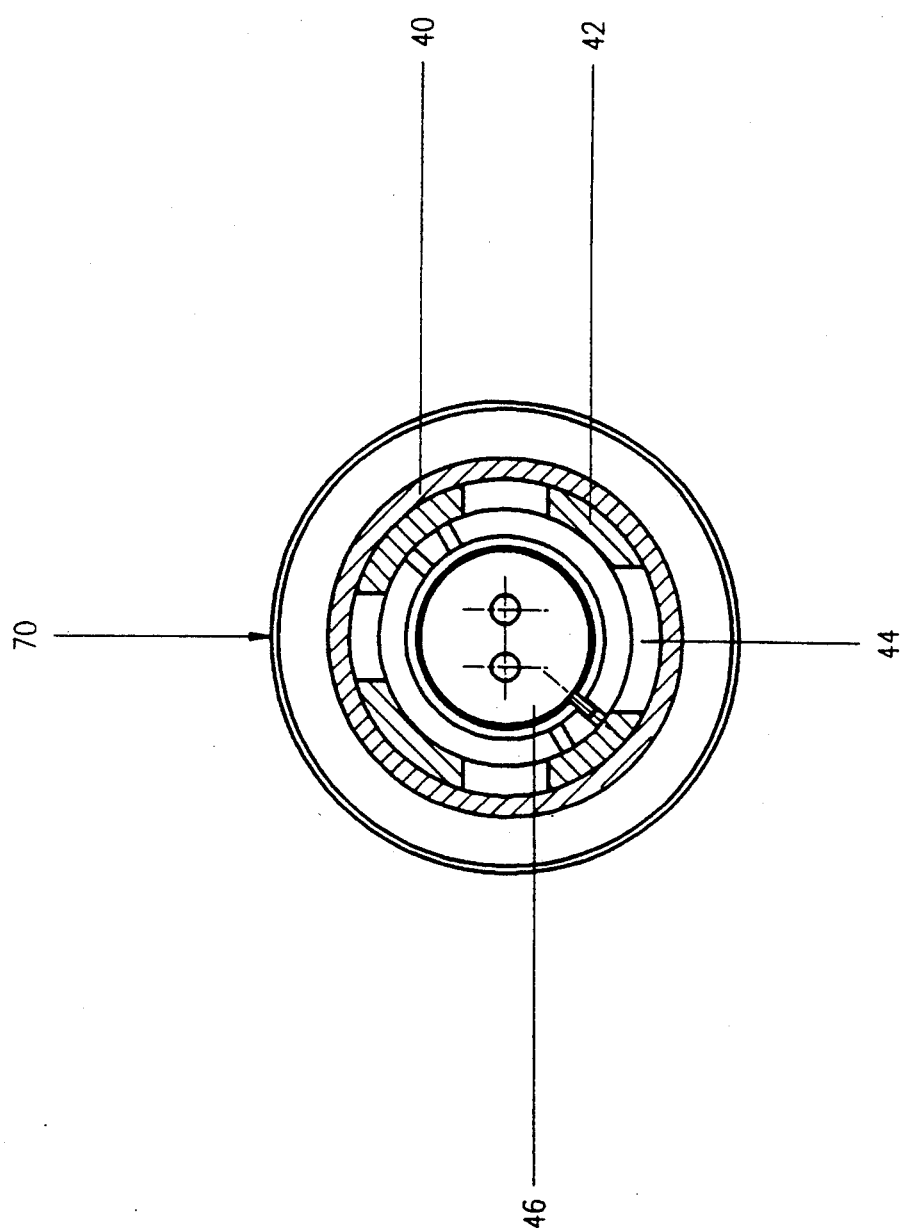
FIG. 4 is a section along the line IV—IV in FIG. 2.

The present invention is embodied in the optical fibre probe shown in detail in FIGS. 2-4. This is designed specifically for attenuated total reflectance (ATR) measurements on non-transmitting fluids and semi-solid samples, typically in the mid infra-red or near infra-red ranges (500 cm$^{-1}$ to 10000 cm$^{-1}$). The ranges stated must not, however, be considered as limiting, as the probe of the present invention may well be used, in appropriate circumstances, with wider ranges.

Figure 1:
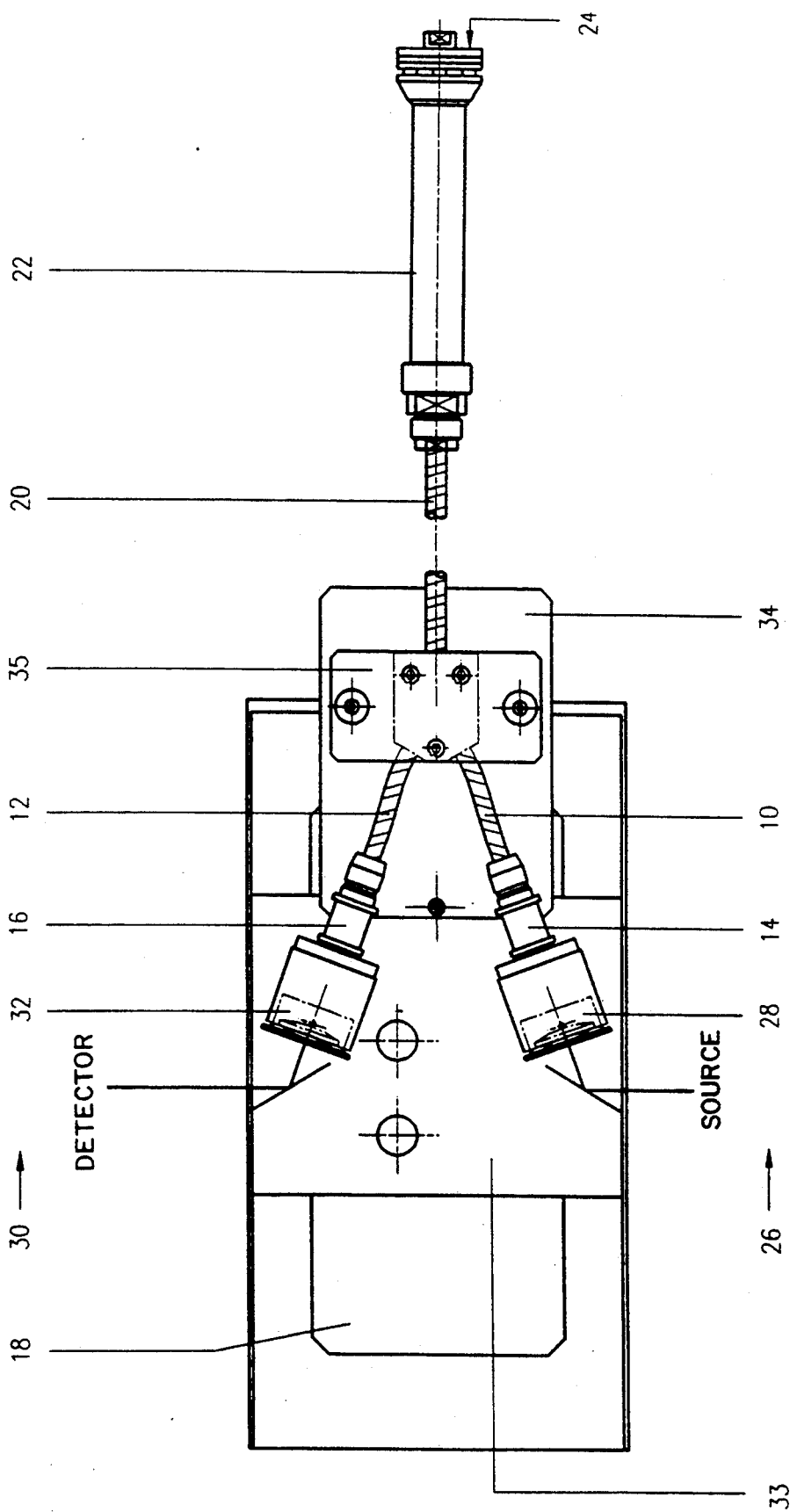
FIG. 1 illustrates diagramatically the interconnection between an optical fiber probe embodying the present invention and an associated spectrophotometer.

FIG. 1 illustrates diagramatically the interconnection between the optical fiber probe and an associated spectrometer.

The sample compartment 18 of a spectrophotometer (not shown) is adapted to receive mounting plates 33,34 to which are secured sheathed outward and return optical fibers 10,12 respectively terminating in connectors 14,16. The connectors are themselves secured to respective lens assemblies 28,32.

The individual optical fibers 10,12 are secured to the plate 34 by clamp 35, and both fibers then continue within a commonly sheathed cable 20 to the transmission probe assembly 22.

Radiation from the source optics 26 of the spectrophotometer passes into fiber 10 via lens assembly 28, is transmitted along the optical fiber 10 to the sampling head 24 of the probe 22, and then returns via the fiber 12 and the lens assembly 32 to the spectrophotometer detector optics 30.

Turning now to the attenuated total reflectance (ATR) probe assembly of FIGS. 2–4, it will be seen that the probe 38 itself has a tubular outer body 40 which contains as a sliding fit within it a tubular sleeve member 42. The sleeve member 42 in turn contains within it as a sliding fit a tubular inner body member 44. The sleeve member 42 is illustrated in more detail in FIG. 7 and the inner body member 44 is shown in more detail in FIG. 6.

The flexible optical fiber cable 20 which contains the optical fibres 10 and 12 enters the probe 38 through a cable clamping collar 68 which is screwed to an end cap 70. The end cap itself is a sliding fit on the outer end of the body 40 and is secured to it by means of a grub screw 72. Sealing between the cable 20 and the end cap 70 is provided by an O ring seal 74. Sealing between the end cap 70 and the body 40 is by means of another O ring seal 76.

The cable 20 continues down inside the inner body member 44 to a collar 78, where the sheathing terminates. The collar 78 is located and held in position in the inner body 44 by means of grub screws 80.

Figure 8B:
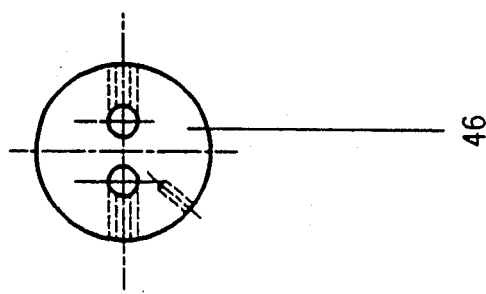
FIGS. 8A and 8B show respectively side elevational and end views of the ferrule plate of the probe of FIG. 1.
Figure 8A:
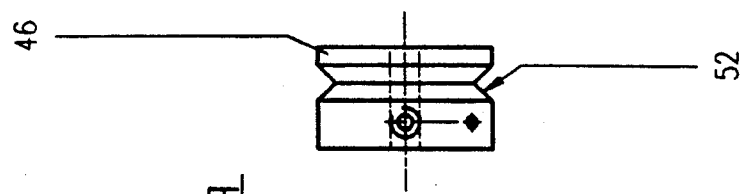

The individual sheathed optical cables 10,12 continue through the collar 78 to a ferrule plate 46 (FIG. 8) which is secured at the end of the inner body member 44 by grub screws 48. The ferrule plate 46 receives and holds in fixed lateral relationship to each other, ferrules 54,56 which terminate the optical fibers 10,12. The ferrules themselves pass through the ferrule plate 46 and are secured by grub screws 58 so as to hold the end faces of the optical fibres in a common plane proud of the end face of the ferrule plate 46. The ferrule plate and its respective grub screws 48 can be used to position the ends of the optical fibers as required, as will be explained in more detail later.

Figure 5:
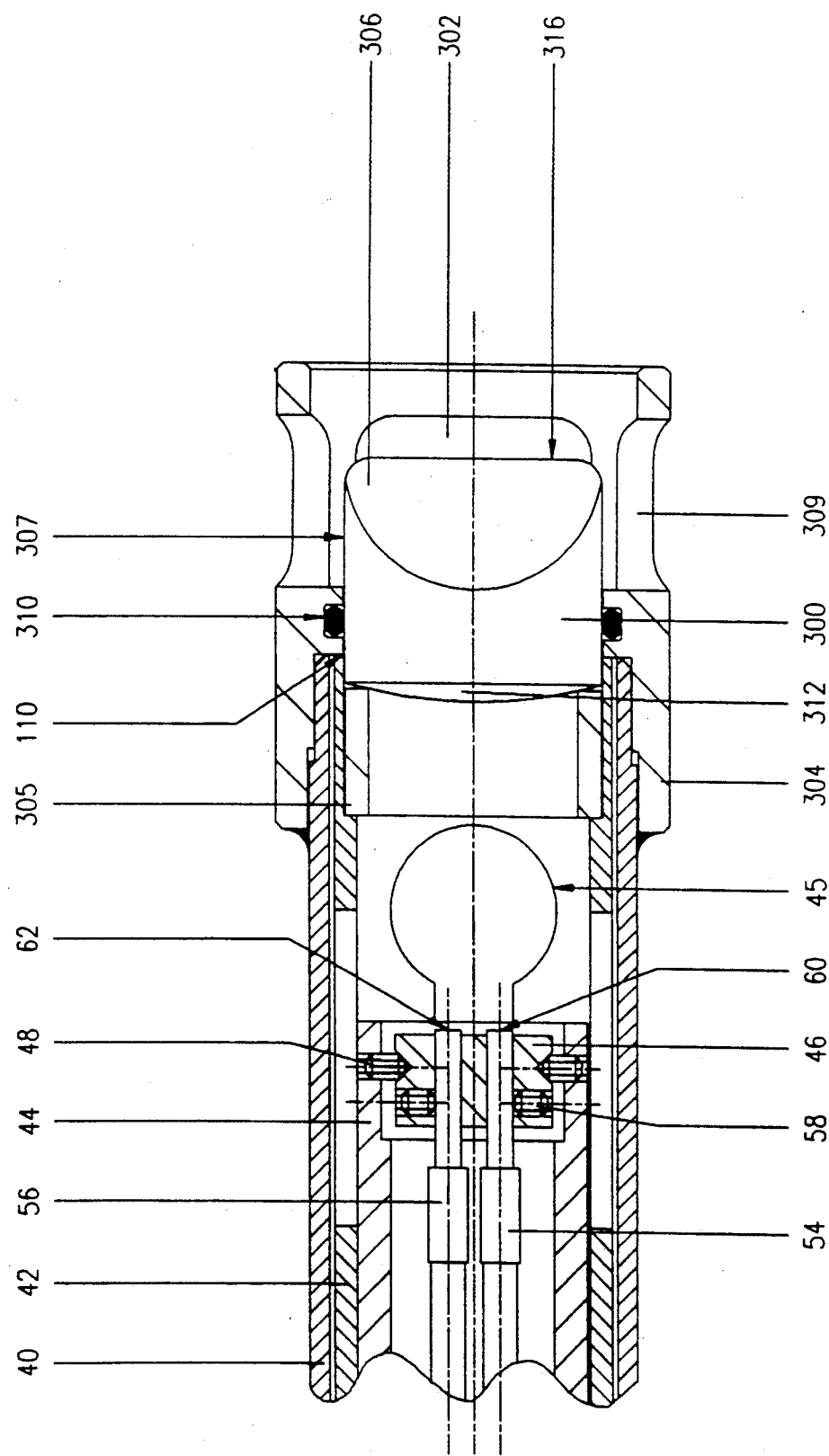
FIG. 5 is an enlarged longitudinal section of one end of the probe of FIG. 1.

The end of the ATR probe of FIG. 2 is shown in enlarged form in FIG. 5, and reference will now be made to that figure.

The far end of the sleeve member 42 is provided with a stepped bore within which is located an annular packing sleeve 305. Closing the end of the sleeve member 42, and located by the packing sleeve 305, is a one piece optical element 300 which provides focusing, collimation and reflection of the radiation beam incoming along the optical fibre 10. The optical element 300 is preferably made from zinc selenide, and has a shape that may be seen more clearly in FIGS. 9A and 9B. The peripheral edge 307 of the element is cylindrical. At one end there is a convex face 312, and at the other two perpendicular cut-away faces 306,308 which meet along a central ridge 316. The element essentially consists therefore of a cylindrical body having at one end a convex face and at the other end a roof prism. The element 300 is preferably 20 mm in diameter and has a total length of about 18 mm, but of course other sizes might be used depending upon the overall size of the ATR probe into which it is fitted. Materials other than zinc selenide, appropriate to the application and to the wavelength of the radiation in use, could also be used.

The element 300, mounted in the end of the sleeve member 42, protrudes into a sample compartment 302 formed in a protective end cap 304 which is welded or otherwise secured to the outer body member 40. The sample compartment has apertures 309 which permit the sample material to enter the compartment when the probe is in use, so coating the outer surfaces 306,308 of the element 300. Sealing between the element 300 and the wall of the end cap 304 is provided by an O ring seal 310; this prevents ingress of sample material into the interior of the probe.

Figure 9B:
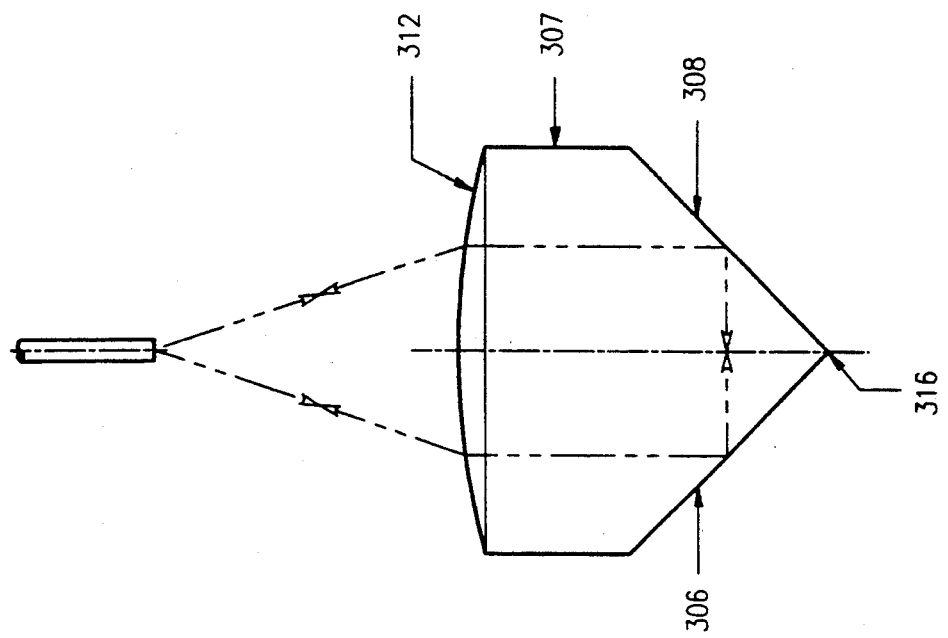
FIGS. 9A and 9B illustrate the optical system of the probe of FIG. 1.
Figure 9A:
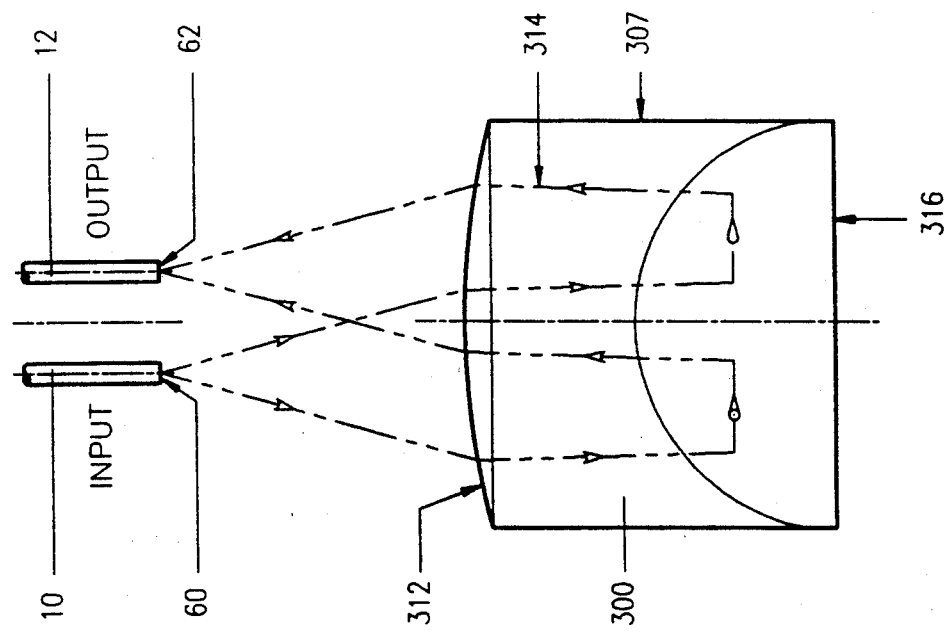

The operation of the probe is best demonstrated by a consideration of FIGS. 9A and 9B. Radiation from the spectrophotometer is sent along the optical fiber 10. Rays emerge from the end face 60 of that optical fiber, and are refracted by the convex face 312 of the element 300 to produce a parallel beam 314 which is incident upon the inner surfaces of the perpendicular faces 306, 308. The radiation is totally internally reflected at those faces and is directed back through the face 312 which focuses the beam upon the end face 62 of the output or return optical fiber 12. The radiation then passes along that fiber back to the spectrophotometer for analysis. When the beam is totally internally reflected on the faces 306,308, it picks up a spectrum which corresponds to the sample material which is at that time in contact with those two faces. Accordingly, the sample may be analysed by a consideration of the differences between the spectrum of the radiation sent out from the spectrophotometer, and that received back.

Employing a single composite reflecting and focusing element 300 eliminates the alignment problems which normally occur between separate elements of an ATR optical assembly. In addition, reflection losses are substantially reduced because of the lesser number of surfaces through which the radiation has to pass.

It will be appreciated that the exact alignment of the element 300 with respect to the ends 60,62 of the optical fibers is critical if the probe is to operate at optimal efficiency. In particular, the ridge 316 of the element 300 should lie in the same plane as the ends 60,62 of the optical fibers. In addition, the ends of the fibers must be so positioned that light emitted from the end 60 is accurately focused back on to the end 62 of the other fiber. The manner in which this is achieved will now be explained.

With the outer body member removed, rotational alignment may be achieved by rotating the inner body member 44, and with it the ferrule plate 46, with respect to the sleeve member 42 which carries the optical element 300. Focusing is achieved by sliding the inner body member longitudinally with respect to the sleeve member 42. While these adjustments are being done the output signal is being measured at the spectrophotometer, and when the correct position has been reached the grub screws 48 are tightened to lock the inner body member 44 in place within the sleeve member 42. As may best be seen in FIG. 7, the sleeve member 42 has longitudinal apertures 43 through which the grub screws 48 may be reached from the outside. The purpose of the enlarged opening 45 (visible in FIGS. 2, 5 and 7) is to enable the person adjusting the device to see the ends 60, 62 of the optical fibers. This simply allows the adjustments to be carried out more easily.

Figure 6C:
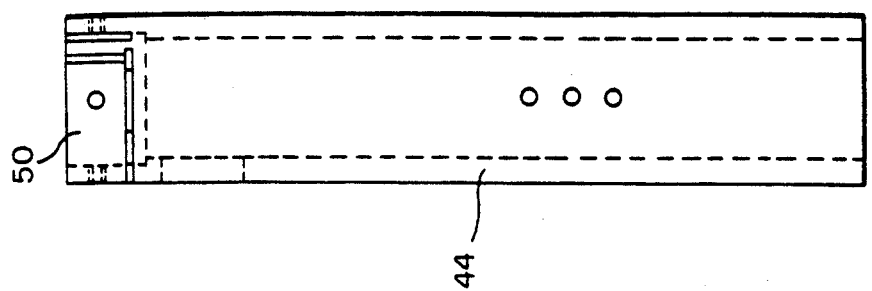
FIGS. 6A, 6B and 6C respectively shows cross-section, plan and side elevational views of the inner body member of the probe of FIG. 1.
Figure 6B:
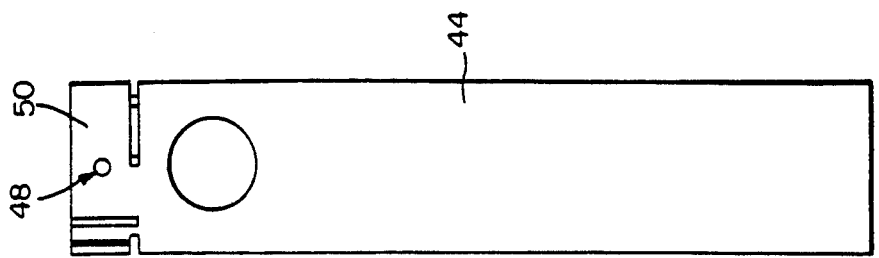
Figure 6A:
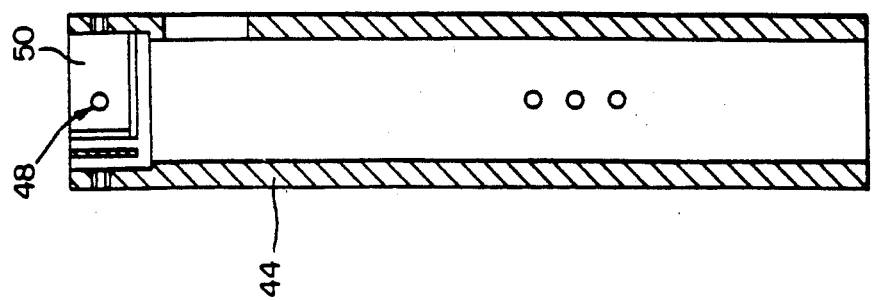
Figure 7A:
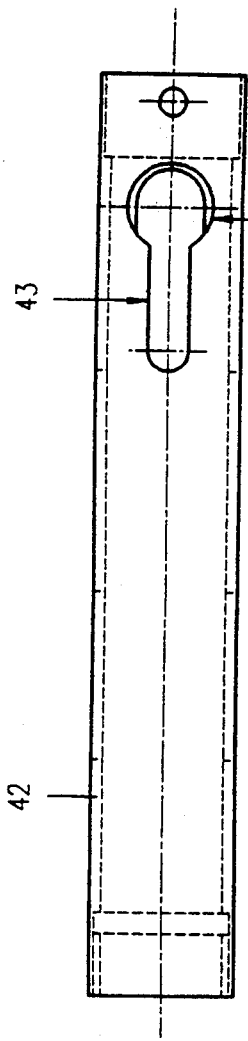
FIGS. 7A, 7B and 7C, show respectively plan, cross-section and bottom views of the sleeve member of the probe of FIG. 1.
Figure 7B:
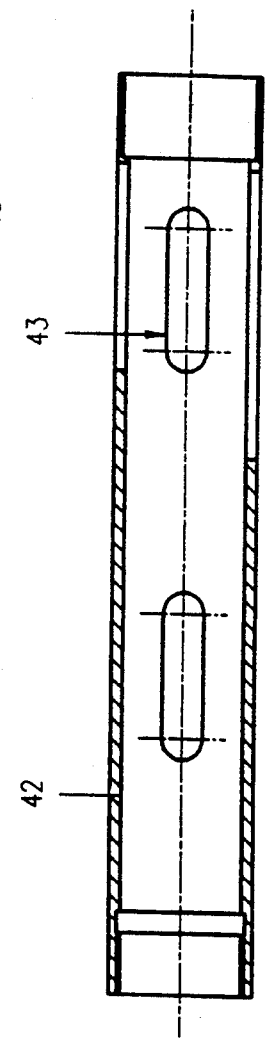
Figure 7C:
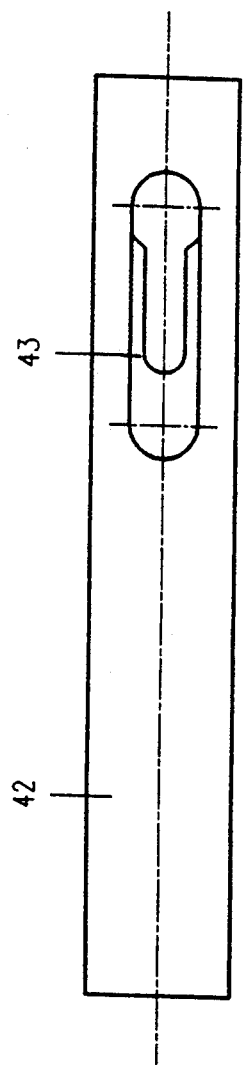

As may be seen in FIG. 6, the grub screws 48 engage in tapped apertures in circumferential tongues 50 formed at the end of the inner body member. The inner ends of these grub screws locate in a circumferential groove 52 of the ferrule plate 46, as may be seen in FIG. 8. Thus, in addition to securing the ferrule plate 46 within the inner body member 44, the grub screws 48 if further tightened deflect the circumferential grooves 50 outwardly to engage the adjacent inner surface of the sleeve member 42, so locking the inner body member and the sleeve member 42 together.

To achieve optimal performance, it may be desired to move the ferrule plate 46 laterally, that is in either of the two directions perpendicular to the axis of the probe. The grub screws 48 may be used for this purpose. Four grub screws are provided, equally spaced around the periphery of the inner body member 44, and if one of these screws is tightened at the same time as the opposite screw is loosened, the ferrule plate will move laterally towards the tightening screw. The plate can of course be moved in the perpendicular lateral direction by tightening and loosening the other pair of grub screws. When the plate is correctly positioned, each pair of opposing grub screws is tightened fully, using two allen keys at once so that one screw is tightened against the other. In this way, the screws can be tightened to secure the inner body member 44 to the sleeve member 42 without altering the lateral position of the ferrule plate 46.

Once focusing and alignment have been achieved, and the grub screws 48 fully tightened to lock the inner body member to the sleeve member, the outer body member 40 is then pushed over the partially completed assembly, with the O ring 310 moving down over the cylindrical surface 307 of the optical element 300. The outer body member 40 can then be secured in position. This is achieved by the combination of insert ring 102, split packing ring 104 and screw ring 106 (see FIG. 2). The insert 102 screws into the upper end of the inner body member 44 and has a shoulder 108 which engages the left hand end of the sleeve 42. In turn, the lower end of the sleeve member 42 engages upon a shoulder 110 at the lower end of the inner body member 44. The split packing ring 104 surrounds the upper part of the insert 102 and has clearance holes in its upper face through which screws 112, mounted in tapped holes in the screw ring 106, pass.

When the screws 112 are tightened upon the insert 102, the lower part of the split packing ring 104 is forced outwardly towards the edges of the wall of the outer body member 40 by means of a wedging action between the insert 102 and the packing ring 104.

This locks the inner body and sleeve assembly to the outer body 40, so enabling the ATR probe 38 to resist longitudinal forces which might be applied in use, for example if the probe is assembled into an aperture in the wall of a pipe line or pressure chamber.

To complete the ATR probe, the end cap 70 is pushed down over the end of the outer body member 40 and secured in position by the grub screws 72.

What is claimed is:

1. An optical fiber probe for remote testing of a sample, said probe including:
   a tubular sleeve member;
   an input optical fiber extending within and longitudinally of said sleeve member and having an end for radiation emission;
   an output optical fiber extending within and longitudinally of said sleeve member and having an end for radiation collection;
   a radiation-transparent optical element, said optical element having a cylindrical side wall, an end face through which said emitted radiation passes, and at least two reflecting surfaces opposite said end face for totally internally reflecting said radiation and redirecting it back through said end face; and
   means for focusing said redirected radiation on to said end of said output optical fiber.

2. An optical fiber probe as defined in claim 1 wherein said reflecting surfaces meet at a central ridge.

3. An optical fiber probe as defined in claim 2 wherein the angle between said two reflecting surfaces at said ridge is 90°.

4. An optical fiber probe as defined in claim 2 wherein said ends of said optical fibers lie in a common plane with said central ridge.

5. An optical fiber probe as defined in claim 4 wherein said reflecting surfaces are planar.

6. An optical fiber probe as defined in claim 1 wherein said reflecting surfaces are planar.

7. An optical fiber probe as defined in claim 1 including collimating and focusing means for collimating said radiation emitted from said end of said input optical fiber and for focusing said redirected radiation on to said end of said output optical fiber.

8. An optical fiber probe as defined in claim 7 wherein said collimating and focusing means is integral with said optical element.

9. An optical fiber probe as defined in claim 7 wherein said end face of said optical element is convex, said convex end face forming said collimating and focusing means.

10. An optical fiber probe as defined in claim 1 wherein said optical element is of zinc selenide.

11. An optical fiber probe as defined in claim 1 wherein said element is configured so that radiation passing through said end face of said optical element over a given range of entry angles is totally internally reflected at said reflecting surfaces and is redirected back through said end face without being reflected from said cylindrical side wall.

12. An optical fiber probe as defined in claim 1 wherein said optical element is secured in an end of said tubular sleeve, with said end surface facing said ends of said optical fibers.

13. An optical fiber probe as defined in claim 12 including O ring seal means around said cylindrical side wall of said optical element to prevent said sample, in contact with said reflecting surfaces, from entering said probe.

14. An optical fiber probe as defined in claim 1 including protective end cap means for protecting said optical element while allowing said sample to reach said reflective surface of said optical element.

15. An optical fiber probe as defined in claim 14 including an external tubular body member, containing said sleeve member, said protective end cap means being secured to said external body member.

16. An optical fiber probe as defined in claim 15 including O ring seal means around said cylindrical side wall of said optical element and providing a seal between said cylindrical side wall and said end cap means.

17. An optical fiber probe as defined in claim 1 including adjustable mounting means for mounting said optical fiber within said sleeve member whereby the position of said ends with respect to said optical element may be adjusted.

18. An optical fiber probe as defined in claim 17 wherein said adjustable mounting means includes an inner tubular body member mounted for sliding adjustment within said sleeve member.

19. An optical fiber probe as defined in claim 18 wherein said inner body member is also mounted for rotational adjustment within said sleeve member.

20. An optical fiber probe as defined in claim 18 wherein said adjustable mounting means includes a mounting block mounted within said inner body member and arranged to hold said ends of said optical fibers at spaced locations.

21. An optical fiber probe as defined in claim 20 wherein said mounting block comprises a ferrule plate, said ferrule plate having ferrules for receiving and locating said ends of said optical fibers.

22. An optical fiber probe as defined in claim 1 wherein said ends of said optical fibers are parallel to each other.

23. An optical fiber probe as defined in claim 22 wherein said ends of said optical fibers lie in the same plane.

24. An optical fiber probe as defined in claim 1 wherein said optical fibers extend generally parallel to each other along the length of said probe.

25. An optical fiber probe as defined in claim 1 wherein said means for focusing includes said end face configured as a convex surface.

26. An optical fiber probe for remote testing of a sample, said probe including:
a tubular sleeve member;
an input optical fiber extending within and longitudinally of said sleeve member and having an end for radiation emission; an output optical fiber extending within and longitudinally of said sleeve member and having an end for radiation collection;
a radiation-transparent optical element, said optical element having a cylindrical side wall, a convex end face through which said emitted radiation passes, and a pair of inclined planar reflecting surfaces, angled at 90° to each other, opposite said end face for totally internally reflecting said radiation and redirecting it back through said convex end face;
said convex end face acting to collimate said radiation emitted from said end of said input optical fiber and to focus said redirected radiation on to said end of said output optical fiber.

27. An optical element made of radiation-transparent material, said element having a cylindrical side wall, a radiation-transparent end face for admitting radiation into said element, and at least two radiation-transparent reflecting surfaces opposite said end face oriented for totally internally reflecting radiation received from said end face and redirecting said received radiation back through said end face.

28. An optical element as defined in claim 27 wherein said reflecting surfaces meet at a central ridge.

29. An optical element as defined in claim 28 wherein the angle between said two reflecting surface at said ridge is 90°.

30. An optical element is defined in claim 29 wherein said reflecting surfaces are planar.

31. An optical element as defined in claim 27 wherein said reflecting surfaces are planar.

32. An optical element as defined in claim 27 wherein said optical element is of zinc selenide.

33. An optical element as defined in claim 26 wherein said element is configured so that radiation passing through said end face over a given range of entry angles is totally internally reflected at said reflecting surfaces and is redirected back through said end face without being reflected from cylindrical side wall.

* * * * *